United States Patent [19]
Hess et al.

[11] Patent Number: 5,948,015
[45] Date of Patent: Sep. 7, 1999

[54] MEDICAL ELECTRICAL LEAD

[75] Inventors: Douglas N. Hess, Maple Grove; Richard D. Sandstrom, Scandia; Michael A. Ruff, Blaine; Rodica V. Ruta, White Bear Lake, all of Minn.

[73] Assignee: Medtronic, Inc., Minneapolis, Minn.

[21] Appl. No.: 09/078,977

[22] Filed: May 14, 1998

[51] Int. Cl.$^6$ .................................................. A61N 1/05
[52] U.S. Cl. ............................................ 607/127; 607/126
[58] Field of Search ................................ 607/126, 127

[56] References Cited

U.S. PATENT DOCUMENTS

| | | |
|---|---|---|
| 4,106,512 | 8/1978 | Bisping . |
| 4,217,913 | 8/1980 | Dutcher . |
| 4,624,265 | 11/1986 | Grassi . |
| 4,624,266 | 11/1986 | Kane . |
| 5,259,394 | 11/1993 | Bens . |
| 5,425,755 | 6/1995 | Doan . |
| 5,456,708 | 10/1995 | Doan et al. . |
| 5,514,173 | 5/1996 | Rebell et al. . |
| 5,531,780 | 7/1996 | Vachon . |
| 5,897,584 | 4/1999 | Herman . |

Primary Examiner—William E. Kamm
Assistant Examiner—Carl H. Layno
Attorney, Agent, or Firm—Reed A. Duthler; Harold R. Patton

[57] ABSTRACT

A medical electrical lead having an electrode head with an internal lumen mounted to a proximal portion of the lead body and a rotatable fixation helix advanceable from the internal lumen. The helix is mounted to a rotatable shaft which is provided with a central shaft portion and circumferential shoulders proximal and distal to the central shaft portion. A seal is mounted in the lumen of the electrode head, encircling the shaft and C-shaped seal retainers are mounted in the lumen of the electrode head member proximal and distal to the seal.

7 Claims, 3 Drawing Sheets

MEDICAL ELECTRICAL LEAD

BACKGROUND OF THE INVENTION

The present invention is directed toward medical electrical leads generally and more particularly directed towards medical leads employing advancable, rotating fixation helixes to anchor the leads to body tissue.

In order to work reliably, cardiac pacing leads need to be located stably adjacent tissue to be stimulated or monitored. One common mechanism for accomplishing this has been the use of a rotatable fixation helix, which exits the distal end of the lead and is screwed into body tissue. The helix itself may serve as an electrode or it may simply serve as an anchoring mechanism to locate an electrode mounted to the lead body adjacent body tissue. In conjunction with such leads, the fixation helix may be coupled to a conductor extending through the lead body and rotated by rotation of the conductor within the lead body. Such a lead is disclosed in U.S. Pat. No. 4,106,512 issued to Bisping. Alternatively, the fixation helix may be rotated by means of a screwdriver tip stylet, or other removable rotation device, as disclosed in U.S. Pat. No. 4,217,913 issued to Dutcher.

Typically, some mechanism is provided for sealing the distal end of the lead against fluid entry. One common mechanism is to provide a seal which engages the fixation helix directly, as disclosed in the above cited Bisping patent. An alternative mechanism, particularly useful in the circumstance in which the helix is mounted to a shaft, either rotated by means of the conductor or by means of a screwdriver stylet is to operatively associate a seal with the helix shaft for preventing the ingress of body fluids, by mounting a washer shaped seal encircling the shaft. The seal may either rotate with the shaft, as disclosed in European Patent Application No. 049431 issued to Borghi et al or the shaft may rotate relative to the seal as disclosed in U.S. Pat. No. 5,259,394 issued to Bens. If the seal rotates with the shaft, the seal may be located between two washer shaped members located on the shaft as in the Borghi patent. If the shaft rotates relative to the seal, the structure may correspondingly be reversed, with the seal located between washer shaped members mounted in the electrode head as in U.S. Pat. No. 5,456,708 issued to Doan. Alternatively, the seal may simply be mounted to the shaft as in U.S. Pat. No. 5,514,173 issued to Rebell or to the interior of the electrode head by adhesive or other means as in the Bens patent and in U.S. Pat. No. 5,425,755 by Doan. Because that portion of the seal which rotates relative to the shaft or relative to the electrode head produces frictional resistance to rotation, it is in some cases desirable to configure this surface as a line contact to reduce friction, as is conventional in the art related to fluid seals associated with rotating shafts and as disclosed in the Borghi et al patent and in the '708 Doan patent.

In the event that it is desired to mount a seal located fixedly within the electrode head, surrounding the helix shaft, as in the Doan patents and the Bens patents cited above, it is necessary to pass the helix shaft through the seal. Similarly, if one wishes to employ washer-shaped members on either side of the seal as in the Bens and Doan '708 patents, the helix shaft must either carry the washer shaped members or must pass through the central apertures in the washer shaped members. This generally is not a problem, except in the context of a shaft which rotates relative to the seal when it is desired that the helix shaft be constructed with enlarged radius shoulders, located on either side of the seal to define advancement and retraction stops. If washer-shaped retainers are to be used as in the Doan '708 patent, the helix shaft must be fabricated out of two separate pieces.

SUMMARY OF THE INVENTION

The present invention is directed toward an improved lead of the type employing an advancable fixation helix mounted to a helix shaft and which rotates relative to a seal encircling the helix shaft. In a preferred embodiment, the helix shaft is provided with enlarged shoulders located proximal and distal to the central portion of the shaft which passes through the seal, which shoulders serve as advancement and retraction stops. The seal is placed around the shaft between the shoulders and is maintained properly located within the electrode head by means of two C-shaped retainers which engage the proximal and distal shoulders of the helix shaft to define positions of maximum advancement and retraction. The C-shaped retainers, in conjunction with the enlarged shoulders on the shaft also provide a mechanism for determining the degree of advancement of the helix and shaft using a fluoroscope. The C-shaped retainers and the seal are placed around the helix shaft prior to the insertion of the helix shaft into the electrode head. By this mechanism, the helix shaft can be fabricated as a single piece part, simplifying manufacture of the lead.

DETAILED DESCRIPTION OF THE PREFERRED EMBODIMENTS

Figure 1:
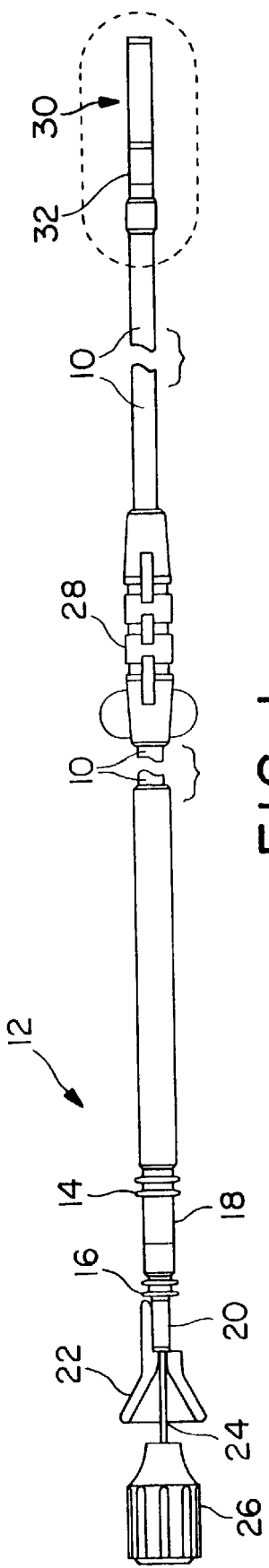
FIG. 1 is a plan view of a lead incorporating the present invention.

FIG. 1 is a plan view of a cardiac pacing lead employing the present invention. The lead is provided with an elongated lead body 10 which takes the form of an extruded tube of biocompatible plastic such as silicone rubber or polyurethane. At the proximal end of the lead is a connector assembly 12 which includes a connector pin 20 and a connector ring 18 which are coupled to coil conductors extending distally therefrom within lead body 10. Sealing rings 14 and 16 are provided to seal the connector assembly in the connector block in an associated implantable cardiac pacemaker and to seal between connector pin 20 and connector ring 18. Exiting the proximal end of the connector pin 20 is a stylet 24, shown exiting through removable stylet guide 22. Stylet knob 26 is provided to assist the physician in moving and turning stylet 24 relative to the lead body 10 in order to assist in placement of the lead at a desired location within a patient's heart. Suture sleeve 28 is provided to assist in anchoring the lead at the point of venous insertion. An electrode head 30 is located at the distal end of the lead, and carries an advanceable fixation helix as described generally above. A ring electrode 32 is mounted proximal to electrode head 30. Electrode 32 is electrically coupled to connector 18 and the advancable fixation helix within electrode head 30 is electrically coupled to connector pin 20. Rotation of connector pin 20 relative to the connector assembly 12 causes corresponding rotation of the coiled conductor coupled thereto and advancement or retraction of the fixation helix within lead 30 in the fashion generally described in U.S. Pat. No. 4,106,512 issued to Bisping et al, incorporated herein by reference in its entirety.

While the lead of FIG. 6 takes the form of a bipolar pacing lead, the present invention may of course be embodied in other types of pacing leads, including unipolar leads and leads with additional electrodes and/or sensors. The invention is also useful in the context of implantable cardioversion and defibrillation leads and in any other circumstance in which it is desirable to affix a lead adjacent to body tissue to stimulate or sense electrical activity in the body, including nerve and muscle stimulation leads and the like.

Figure 2:
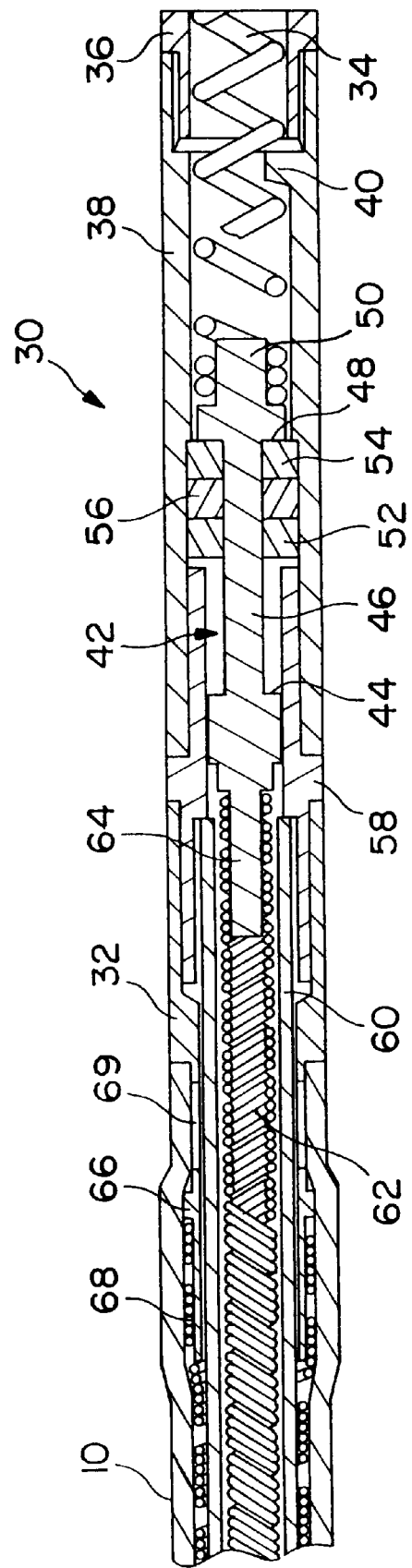
FIG. 2 is a cut-away view through the distal portion of the lead illustrated in FIG. 1.

FIG. 2 is a cut-away view through the distal portion of the lead of FIG. 1. Lead body 10 in this view is seen to be an elongated extruded tube of biocompatible plastic, which surrounds two coaxially arranged coiled conductors 62 and 68, each of which take the form of multifilar coils of biocompatible metal such as MP35N alloy, drawn brazed strand wire, or other conductors conventionally employed in implantable stimulation leads. Separating conductors 62 and 68 is an inner insulative sheath 60 which also takes the form of an extruded tube of biocompatible plastic such as polyurethane or silicone rubber. Ring electrode 32 is fabricated of a biocompatible metal such as stainless steel or platinum/iridium alloy and is coupled to coiled conductor 68 by means of a weld adjacent the circumferential flange 66 located on the proximal portion of the ring electrode. A cross bore 69 through a ring electrode 32 is provided to allow for backfilling to bond the distal portion of lead body 10 to the inner insulative sheath 60 and thereby providing a mechanical interlock.

Mounted to the distal end of ring electrode 32 is an electrode head assembly 30. Electrode head assembly 30 includes a main head member 38 which takes the form of a generally tubular molding of rigid, biocompatible plastic, such as a polyurethane, a proximal head member 58 which also is a generally tubular molding of biocompatible plastic and a distal head member 36, molded of biocompatible silicone rubber, polyurethane or other biocompatible plastic, containing a steroid, for example a form of dexamethasone which will elute from the plastic. Mounted within the internal lumen within the electrode head 30 is an advanceable fixation helix 34 which is fabricated of a biocompatible metal such as platinum/iridium alloy and serves as the pacing electrode. Helix 34 engages inward projection 40 in a fashion such that upon rotation of helix 34, it is either screwed into or out of the distal opening in distal head member 36. The proximal end of fixation helix 34 is coupled to the distal portion 50 helix shaft 42. The proximal end 64 of shaft 42 is in turn coupled to coiled conductor 62, such that upon rotation of coil conductor 62, fixation helix 34 rotates relative to protrusion 40, causing it to be screwed into out of electrode head assembly.

Mounted around the central portion 46 of helix shaft 42 is a resilient seal 56 which may be molded of a biocompatible plastic such as silicone rubber or polyurethane. The internal bore of seal 56, through which helix shaft 42 passes is essentially cylindrical. Located on either side of seal 56 are C-shaped retaining members 52 and 54 visible in cross-section. These retaining members are preferably fabricated of a biocompatible radiopaque metal such as platinum or platinum-iridium alloy and serve both to locate seal 56 in the electrode head and as proximal and distal stops, limiting proximal and distal movement of helix shaft 46. The distal portion of the outer surface of the seal 56 is conically tapered, which allows a wider range of tolerances for the components of the electrode head assembly and simplifies assembly when the helix shaft 42, seal 56 and seal retainers 52 and 54 are slid distally into head member 38. As shown, helix 34 is fully retracted into the electrode head assembly, with the enlarged circumferential distal shoulder 48 of the helix shaft abutting C-shaped seal retainer 54. When fully extended, the enlarged proximal circumferential shoulder 44 of shaft 42 abuts C-shaped seal retainer 52. C-shaped seal retainers 52 also serve as radiopaque indicators, having fixed locations relative to the electrode head assembly 30, which allows the physician to determine the relative degree of advancement of helix 34 by comparing the relative locations of the C-shaped retainers 52 and 54 and helix shaft 42.

The use of C-shaped seal retainers 52 and 54 in conjunction with a resilient seal 56 allows the seal and retainers to first be located around the central shaft portion 46 and assembly thereafter to be advanced into the main electrode head member 38. The proximal electrode head member 58 can then be inserted into the proximal end of the main electrode head member 38 and bonded thereto by means of adhesive or otherwise, retaining the assembly of helix shaft 42, retainers 52 and 54 and seal 56 within the electrode head assembly 30.

Figure 3:
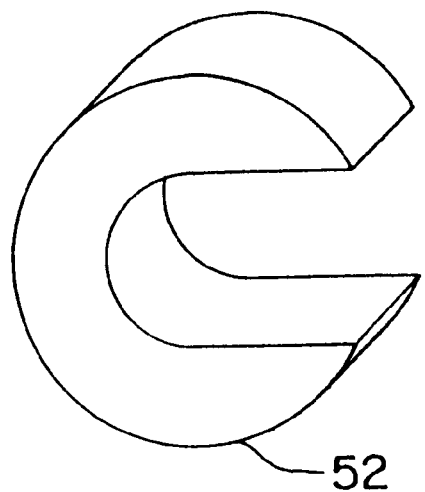
FIG. 3 is a perspective view of one of the C-shaped seal retainers employed in the lead of FIGS. 1 and 2.

FIG. 3 is a perspective viewing of one of the two retainers 52, illustrating its C-shaped configuration.

Figure 4:
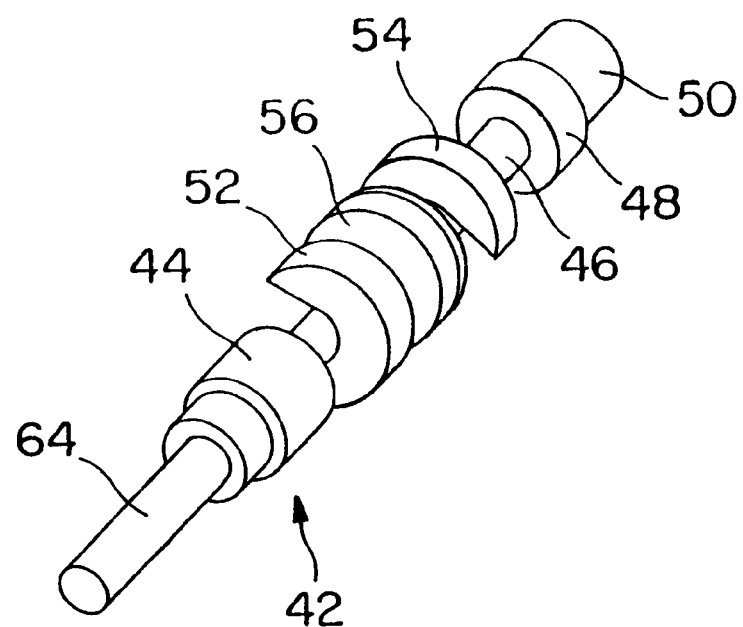
FIG. 4 is a perspective view of the helix shaft of the lead of FIGS. 1 and 2, shown with the seal and two C-shaped seal retainers mounted thereto.

FIG. 4 is a perspective view of the helix shaft 42, seen generally from its proximal end, with seal 56 and C-shaped retainers 52 and 54 located thereon, prior to insertion of the assembly into the electrode head. It should be understood that prior to insertion of this assembly into the electrode head, the fixation helix would be attached to the distal portion 50 of shaft 46 and the coiled conductor 62 would be attached to the proximal end 64 of the helix shaft. The resilient seal is seal expanded, slipped over one of the two shoulders 44 and 48 on the helix shaft and placed around the central shaft portion 46 of the helix shaft 42. C-shaped retainers are shown located facing oppositely with respect to one another, although this is not necessary for the assembly to function properly and are mounted on either side of the seal, along the central shaft portion 46. Use of the C-shaped retainers in conjunction with the split seal allows shaft 42 to be fabricated as a single piece part, simplifying manufacture and assembly of the lead.

While the above-described embodiment of the invention describes a lead in which the fixation helix serves as an electrode, it should be understood that the invention may also be usefully be practiced in leads in which the helix serves only for fixation and a separate electrode is provided as in U.S. Pat. No. 4,217,913, issued to Dutcher et al. and incorporated by reference in its entirety herein. Similarly, while in the disclosed embodiment, a coiled conductor is employed to rotate the fixation helix, the invention may also be usefully be practiced in leads in which a removable stylet is employed to rotate the helix as in the Dutcher '913 patent. As such, the above described embodiment should be considered illustrative rather than limiting in conjunction with the following claims.

In conjunction with the above specification, we claim:

1. A medical electrical lead, comprising:
   an elongated lead body having proximal and distal ends and carrying an elongated conductor therein;
   an electrode head member having an internal lumen, mounted to a proximal portion of the lead body;
   a shaft, having proximal and distal ends, rotatably mounted in the head member;
   a fixation helix, mounted to the distal end of the shaft;
   a seal, mounted in the lumen of the electrode head member, encircling the shaft; and
   C-shaped members mounted in the lumen of the electrode head member proximal and distal to the seal.

2. A lead according to claim 1, wherein the shaft is provided with circumferential shoulders proximal and distal to the C-shaped members.

3. A lead according to claim 2 wherein the conductor is rotatably mounted in the lead body and is coupled to the helix shaft.

4. A lead according to claim 1 wherein the conductor is rotatably mounted in the lead body and is coupled to the helix shaft.

5. A lead according to claim 1 wherein the C-shaped members are fabricated of radiopaque material.

6. A lead according to claim 5, wherein the shaft is provided with circumferential shoulders proximal and distal to the C-shaped members.

7. A lead according to claim 1 wherein the outer surface of the seal is tapered.

* * * * *